(12) United States Patent
Nosrati (10) Patent No.: US 9,889,236 B2
(45) Date of Patent: Feb. 13, 2018

(54) SCALABLE MICROFLUIDIC BASED ARTIFICIAL SKIN

(71) Applicant: Micromedics Inc., Tarzana, CA (US)

(72) Inventor: Saeid Mordechai Nosrati, Tarzana, CA (US)

( * ) Notice: Subject to any disclaimer, the term of this patent is extended or adjusted under 35 U.S.C. 154(b) by 128 days.

(21) Appl. No.: 15/060,485

(22) Filed: Mar. 3, 2016

(65) Prior Publication Data
US 2017/0252488 A1 Sep. 7, 2017

(51) Int. Cl.
| | |
|---|---|
| *A61L 27/60* | (2006.01) |
| *A61L 27/54* | (2006.01) |
| *A61L 27/18* | (2006.01) |
| *A61L 27/56* | (2006.01) |
| *A61L 27/26* | (2006.01) |
| *A61L 27/22* | (2006.01) |
| *A61L 27/34* | (2006.01) |
| *A61F 13/02* | (2006.01) |
| *A61M 35/00* | (2006.01) |
| *A61F 13/00* | (2006.01) |

(52) U.S. Cl.
CPC ............ *A61L 27/60* (2013.01); *A61F 13/022* (2013.01); *A61F 13/0216* (2013.01); *A61F 13/0226* (2013.01); *A61L 27/18* (2013.01); *A61L 27/22* (2013.01); *A61L 27/26* (2013.01); *A61L 27/34* (2013.01); *A61L 27/54* (2013.01); *A61L 27/56* (2013.01); *A61M 35/00* (2013.01); *A61F 2013/0017* (2013.01); *A61F 2013/00285* (2013.01); *A61L 2300/104* (2013.01); *A61L 2300/404* (2013.01); *A61L 2300/412* (2013.01); *A61L 2300/608* (2013.01); *A61L 2420/08* (2013.01); *A61L 2430/16* (2013.01); *A61L 2430/34* (2013.01); *A61M 2202/0208* (2013.01)

(58) Field of Classification Search
CPC .... A61L 27/60; A61F 13/022; A61F 13/0216; A61F 13/0226
See application file for complete search history.

(56) References Cited

U.S. PATENT DOCUMENTS 8,764,732 B2 * 7/2014 Hartwell ........... A61F 13/00068
604/317

* cited by examiner

*Primary Examiner* — Thomas J Sweet
*Assistant Examiner* — Daniel Bissing
(74) *Attorney, Agent, or Firm* — Elizabeth Yang (57) ABSTRACT

A scalable microfluidic based artificial skin covers a variety of wounds while also providing efficient healing of the wounds. The artificial skin comprises a plurality of microfluidic panels separated by semi-permeable membranes, and also comprising a plurality of micro-pumps and micro-channels for carrying healing fluids in proximity to the wound on the natural skin. The panels form detachable patches that are inert and biocompatible. The panels are fabricated from polydimethylsiloxane materials and impregnated with silver nanocrystalline powder. A first panel partially engages the natural skin, partially supported by micropillars. Large micro-channels carry contaminants from the wound. A second panel and an optional third panel having micro-channels that carry healing fluids to the wound. A first and second semi-permeable membrane regulate passage of fluids, cellular components, and debris between the panels. An inlet port enables passage of healing fluids to the wound. An outlet port enables discharge of contaminants.

25 Claims, 6 Drawing Sheets

SCALABLE MICROFLUIDIC BASED ARTIFICIAL SKIN

FIELD OF THE INVENTION

The present invention relates generally to a scalable microfluidic based artificial skin for covering a variety of wounds while also providing efficient monitoring, treating and healing of the wounds. More so, a scalable microfluidic based artificial skin covers a variety of wounds while also providing efficient healing of the wounds; whereby the artificial skin comprises a plurality of microfluidic panels separated by semi-permeable which may have different physical and chemical characteristics, porosities and molecular weight cut off MWCO values, and also comprising a plurality of micro-pumps and micro-channels for carrying treatment fluids and solutions including but not limited to antibiotics, analgesics, both macro- and micro-nutrients growth factors and oxygen in proximity to the wound on the natural skin; whereby the panels form detachable patches that are inert and biocompatible; whereby the panels are fabricated from inert and biocompatible compounds used in microfluidics such polydimethylsiloxane materials and optionally impregnated with silver nanocrystalline powder; whereby a first panel partially engages the natural skin, partially supported by micro-pillars; whereby a plurality of large micro-channels carry contaminants from the wound; whereby a second panel and an optional third panel have micro-channels that carry treatment fluids and solutions including but not limited to antibiotics, analgesics, both macro- and micro-nutrients growth factors, oxygen, and etc. to the wound; whereby a first and second semi-permeable membrane which may have different physical and chemical characteristics, porosities and molecular weight cut off MWCO values regulate passage of fluids, cellular components, and debris between the panels; whereby at least one inlet port enables passage of different types of fluids and solutions required for improved healing the wound such as treatment fluids and solutions including but not limited to antibiotics, analgesics, both macro- and micro-nutrients growth factors, and oxygen; whereby at least one outlet port enables discharge of contaminants and cellular debris.

Furthermore, this artificial skin may optionally be used to perform micro-dialysis. The semipermeable membrane (detailed characteristics) used for local wound care and local microdialysis function of comes in direct contact with the soft tissue. The device is connected to a reservoir of biologically sterile dialysate fluid which could have different compositions as needed, which can be programmed to perform local dialysis at the level of the wound. The device is perfused with a sterile isotonic solution of different balance and pH adjusted electrolyte solutions via a small pump attached to its inlet lumen. In the tissue, substances from the interstitial fluid diffuse through the semi-permeable membrane which may have different physical and chemical characteristics, porosities and molecular weight cut off MWCO values into the perfusion fluid. The dialysate moves through the microfluidic channels of the device and into a collection reservoir.

Additionally, this artificial skin may be combined with Cold-Plasma Technology to deliver reactive oxygen and nitrogen species for better and faster wound healing while providing antimicrobial conditions for cleaner and more sterile wound environment.

BACKGROUND OF THE INVENTION

Typically, artificial skin involves application of a collagen scaffold that induces regeneration of skin, specifically for mammals. Treatment of deep skin wounds in adult animals and humans with this scaffold induces regeneration of the dermis. In one commercial embodiment, the artificial skin has been developed commercially under the name Integra™ and is used in massively burned patients, during plastic surgery of the skin, and in treatment of chronic skin wounds.

It is known that successful wound care involves optimizing patient local and systemic conditions in conjunction with an ideal wound healing environment. Many different products have been developed to influence this wound environment to provide a pathogen-free, protected, and moist area for healing to occur. Newer products are currently being used to replace or augment various substrates in the wound healing cascade.

The current state of the art in wound-healing products are applications of antimicrobial silver compounds such as microbial prophylaxis and treatment, negative pressure wound devices, advanced dressings and skin substitutes, biologic wound products including growth factor applications, and hyperbaric oxygen as an adjunct in wound healing. Unfortunately each one of these products addresses only limited factors involved in wound healing and repair. With the design of this novel product, product will bring all these products plus other unique innovations into one single device to provide optimum environment for the proper and rapid wound healing of even non-healing wounds. The present invention is an easily applicable skin barrier with the combination of many of the uniquely designed modalities to optimize wound healing.

Other proposals have involved artificial skin graphs and patches. The problem with these artificial skins is that they do not enable microfluidic characteristics, and the fluids cannot be recorded.

Thus, there are several unmet and unaddressed needs exist in the industry to address the aforementioned deficiencies and inadequacies. Even though the above cited skins meet some of the needs of the market, a scalable microfluidic based artificial skin comprising single or multiple layers of panels fabricated from different inert and biocompatible polymers such as polydimethylsiloxane (PDMS) with microfluidic micro-channels for covering a variety of wounds while also providing efficient healing of the wounds is still desired.

The present invention also utilizes cold micro-plasma capability. Those skilled in the art will recognize that Plasma is one of the four fundamental states of matter, the others being solid, liquid, and gas. Plasma has properties unlike those of the other states. Plasma can be created by heating a gas or subjecting it to a strong electromagnetic field applied with a laser or microwave generator. This decreases or increases the number of electrons, creating positive or negative charged particles called ions, and is accompanied by the dissociation of molecular bonds, if present. The presence of a significant number of charge carriers makes plasma electrically conductive so that it responds strongly to electromagnetic fields. Like gas, plasma does not have a definite shape or a definite volume unless enclosed in a container. Unlike gas, under the influence of a magnetic field, it may form structures such as filaments, beams and double layers. Plasma technology could be effective against pathogenic bacteria with multiple-antibiotic resistance. Another great advantage to cold plasma therapy is that it is non-specific, meaning it is much harder for bacteria to develop resistance. It's a method that is contact free, painless.

Cold plasmas are partially ionized gases, that means only one particle out of $1 \times 10^9$ is ionized. The advantage of cold atmospheric plasmas is that they are "cold", within the meaning that they operate under room temperature and can be produced at atmospheric pressure on Earth. Cold plasmas with temperatures of 35-40° C. make the technology an attractive option for treating infections. Cold plasmas are able to kill bacteria by damaging microbial DNA and surface structures without being harmful to human tissues. Importantly, it has been shown that plasma is able to kill bacteria growing in biofilms in wounds, although thicker biofilms show some resistance to treatment.

Use of cold plasmas in biology and medicine has recently gained significant interest. One of the most widely discussed potential applications is plasma treatment of infections and wounds for the purpose of reducing microbial load and enhancing healing processes. Lately, the significance of cold plasma (ions, electrons) and ultimately the role of the Reactive Oxygen and Nitrogen Species (RONS) generated in this manner in wound healing have been recognized globally. To this end, there has a great deal of experimentation and exploring by many scientists all over the world. There are currently two German devices that have received European approval of CE Marking. (the equivalent of FDA approval in the US) for chronic wound healing applications. In addition, there is a long history of O3 as a wound healing agent, especially for slowly healing war wounds, dating back to WWI and WWII.

Two major types of plasma treatment have been used in wound disinfection and sterilization. One is indirect treatment using gas flow through plasma which brings mostly neutral active species in contact with living tissue. The other is direct application of non-thermal plasma to living tissues. Indirect treatment permits to decouple plasma system design from constraints related to applying the treatment to living tissues. For example, it permits to employ thermal plasma for generation of active species including substantial quantities of NO.

In direct plasmas the tissue/skin itself serves as an electrode so that in this form current flows through the body. A common example of this is the "dielectric barrier discharge" device (DBD). These discharges are termed barrier discharges, because the electrodes are separated by a non-conducting layer (barrier). The discharges are then not "massive" and possibly catastrophic as in lightning, but "gentle"—in many small micro-discharges of about 100 nanoseconds duration—from the barrier to the opposite electrode. On average an almost homogeneous "carpet" of discharges results—assuming that the distances to the opposite electrode are exactly equal. Typically, the distance between the plasma device and tissue is 1 mm.

Indirect plasmas are produced between two electrodes and then transported to the target area by a gas flow. The individual discharge can be markedly stronger here since there is no interference by a barrier, the transport of the charge carriers and the produced molecules away from the discharge region results simply from the gas flow and from diffusion. Most devices of this type produce thin mm diameter plasma jets, larger surfaces can be treated simultaneously by joining many such jets or by multi-electrode systems. Significantly larger surfaces can be treated than with direct plasmas. Further, the distance between the device and the skin is to a certain degree variable, as the skin is not needed as a plasma electrode, significantly simplifying use on the patient.

It should be pointed out that although O3 has been used in the past and is continued to be used throughout the world (in various forms) for wound treatment (among other applications), the use of controlled microfluidic devices has not been explored. The possibility of using embedded sensors and combining plasma action with other drugs or treatment modalities that have been developed for microfluidic devices makes this a very promising new direction.

SUMMARY OF THE INVENTION

The present invention is directed to a scalable microfluidic based artificial skin for covering a variety of wounds while also providing easily achieved continuous visual monitoring, supportive care and treatment, and ultimately efficient healing of the wounds. The artificial skin is comprised of a plurality of microfluidic panels separated by semi-permeable membranes which may have different physical and chemical characteristics, porosities and molecular weight cut off MWCO values, and also comprising a plurality of micro-pumps and micro-channels for carrying treatment fluids and solutions including but not limited to antibiotics, analgesics, both macro- and micro-nutrients growth factors, oxygen, etc., and solutions including but not limited to antibiotics, analgesics, both macro- and micro-nutrients growth factors, oxygen, etc. in proximity to the wound on the natural skin, and concomitantly carrying away and removal of the contaminants and wound debris from the wound.

In some embodiments, the artificial skin may include a single or plurality of microfluidic panels that serve as detachable patches over the wounds of natural skin. The panels are generally manufactured from special inert and biocompatible polymers such as PDMS. The panels are fabricated from such polymers as PDMS materials that are optionally impregnated with silver nanocrystalline powder or other antimicrobial agents, which imparts antibacterial properties to the artificial skin device. The panel(s) are disposed in a layered configuration, whereby each panel performs an independent function for healing the wound. The panels have microfluidic components for enhanced transmission of fluids and enablement of efficient wound healing.

In one embodiment, a first panel engages the skin and utilizes a plurality of large micro-channels that carry away contaminants and cellular debris and components away from the wound to improve healing. The first panel further comprises a plurality of micro-pillars (these micro-pillars have the same height but their height can range from 10-100 microns that partially elevate the first panel off the natural skin to allow space for irrigation via different fluids and solutions as well as cell growth while the natural skin is healing. A second panel is disposed adjacent to, and coplanar to the first panel. The second panel includes a plurality of small micro-channels. The small micro-channels work to irrigate and oxygenate the wound by carrying desired and required treatment fluids and solutions including but not limited to antibiotics, analgesics, both macro- and micro-nutrients growth factors, oxygen, etc., and solutions to the wound. A first semi-permeable membrane which may have different physical and chemical characteristics, porosities and molecular weight cut off MWCO values separates the first and second panels, and inhibits passage of cellular components and debris there between. An optional third panel is disposed adjacent to and coplanar to the second panel. A second semi-permeable membrane which may have different physical and chemical characteristics, porosities and molecular weight cut off MWCO values separates the second and third panels, and enables passage of selective molecules, compounds and non-cellular components between the second panel and the third panel.

In some embodiments, a first and second semi-permeable membrane which may have different physical and chemical characteristics, porosities and molecular weight cut off MWCO values regulate passage of fluids, cellular components, and debris between panels. A plurality of micro-pumps and micro-channels carry irrigation fluids, oxygen, and healing components through the artificial skin. Further, the artificial skin device can keep track of treatment fluids and solutions including but not limited to antibiotics, analgesics, both macro- and micro-nutrients growth factors, oxygen, etc., and loses. To optimize wound healing, the treatment fluids and solutions including but not limited to antibiotics, analgesics, both macro- and micro-nutrients growth factors, oxygen, etc. may be warmed up to desired temperature.

In one exemplary use of the artificial skin, the artificial skin can be used for soldiers and fighters at the forefront who can have complicated wounds that require a fast and efficient coverage to stabilize and start to treat the wound with minimal supportive caregivers such is the condition in frontline.

Furthermore, the artificial skin is effective for covering a variety of wounds, and especially a burn wound, while also providing efficient healing of the non-healing wounds. The artificial skin is scalable and provides a protective barrier and covering for many types of wounds while providing many features that are designed to promote and enhance the wound healing processes. The artificial skin can be easily applied to a burn wound and maintained using several engineering solutions such as vacuum generation at the borders and other simple yet innovative processes. By applying this artificial skin, a provider may achieve the following goals which are vital for the rapid and complete wound healing. These objectives are as follows:

One objective of the present invention is to provide a microfluidic based artificial skin that helps cover and heal wounds.

Another objective is to provide a protective barrier from the environment

Another objective is to prevent evaporation by occlusive and pressurized yet non-adhering barrier.

Yet another objective is to prevent serum oozing/loss of precious proteins as a result of forming a protective barrier from the environment.

Yet another objective is to prevent major fluid loss in case of moderate to major burns.

Yet another objective is to provide a safe antibacterial environment

Yet another objective is to increase local self-debridement

Yet another objective is to provide temperature control

Yet another objective is to provide pain control via topical and non-systemic pain killers.

Yet another objective is to prevent protein losses and ultimately protein malnutrition as a result of preventing evaporation by occlusive and pressurized yet non-adhering barrier.

Yet another objective is to prevent complicated wound healing as a result of providing pain control via topical and non-systemic pain killers which requires daily bandage and dressing changes which interrupts the process of healing by injuring the tissue regeneration.

Yet another objective is to provide nutritional support via infusion of a balanced electrolyte containing macro and/or micro-nutrients such as glucose, vitamins and amino acids.

Yet another objective is to provide continuous/intermittent varying level of oxygen to the wound bed as required using the unique positive pressure wound care.

Yet another objective is to provide special and controlled way of seeding the wound with skin cells as desired Yet another objective is to provide special and controlled way of administering different types of growth factors required for optimal healing.

Yet another objective is to minimize the disruptive and damaging process of frequent bandage removal and reapplication.

Yet another objective is to provide ease of application.

Yet another objective is to provide the scalability to deal with multiple wounds with different sizes Yet another objective is to provide very accurate fluid losses and gains Yet another objective is to provide a clear and transparent view of the wound bed without the need for barrier/bandage removal and allow continuous visual monitoring of wound.

The artificial skin device utilizes the cutting-edge and highly advanced microfluidic technology which allows it to not only be portable, but have a significantly smaller size and footprint. Furthermore, this scalable and adjustable skin barrier, allows for a close monitoring of the wound via its transparent nature, and allow strict management of fluids and other modalities that are required for wound maintenance and proper repair.

In addition, using microfluidic micro channels and valves, that are bio-mimetically designed would allow the treating healthcare providers to keep the wound constantly covered and uninterrupted while also retaining the capacity to remove fluid if necessary. Further fluids can be infused for continuous or intermittent irrigation. Additionally the artificial skin has the ability to automatically measure inflow and outflow for precise fluid management, prevent loss of invaluable and precious vital serum proteins from the wound bed by applying a positive pressure at the site of the wound negating the hydrostatic pressure in the exposed capillaries. This will also enable keeping the wound area moist at all times.

The artificial skin is fabricated from different inert and biocompatible polymers and compounds used in manufacturing microfluidics such as a polymeric organosilicon compound, like Polydimethylsiloxane (PDMS). PDMS is inert and biocompatible material, belonging to a group of polymeric organosilicon compounds that are commonly referred to as silicones. PDMS is optically clear, and, in general, inert, non-toxic, and non-flammable. The PDMS optionally maybe impregnated with nanocrystalline silver, which gives the artificial skin a property to prevent bacterial growth. Of course, these polymers can be impregnated with other forms of antibacterial compounds as desired.

The first panel of the artificial skin is fabricated from different inert and biocompatible polymers and compounds used in manufacturing microfluidics such as PDMS impregnated with silver PDMS. Though the nano crystalline silver impregnated PDMS is optional. In some embodiments, the first panel may have specially designed micro-pillars with specified width and length that extrude from the surface to keep the surface of this layer just slightly above the wound bed to allow the cells and debris to flow through the large micro-channels. The formed micro-projections are in contact with the wound bed and are the true point of contact between the wound and the artificial skin. Thus, the first panel utilizes the specialized large micro-channels (still micron size) to create a wider channels for debridement.

The first panel may also be used as a trap for the cellular elements of the serosanguinous fluid and have a special inlet and outlet that can be used to exert a slight to neutral negative pressure (or positive pressure if needed) for the accumulation of these cellular debris and components. In addition, this inlet and outlet could be used to periodically wash the cellular and debris away from the site of the wound via flushing with a pH balanced isotonic solution such as lactated ringers or sodium bicarbonate or any other types of solution/fluid desired.

The second panel of the artificial skin is disposed adjacent and coplanar to the first panel. The second panel is fabricated from different inert and biocompatible polymers and compounds used in manufacturing microfluidics such as PDMS. The second panel comprises a plurality of small micro-channels that have different dimensions and aspect ratios that could be larger or smaller than the large micro-channels in the first panel. The small micro-channels work to irrigate and oxygenate the wound. A first semi-permeable membrane which may have different physical and chemical characteristics, porosities and molecular weight cut off MWCO values (with different characteristics, porosity and desired MWCO separates the second panel from the first layer. The first semi-permeable membrane which may have different physical and chemical characteristics, porosities and molecular weight cut off MWCO values (with different characteristics, porosity and desired MWCO) inhibits passage of the cells and debris between the first and second panel. In one embodiment, the first semi-permeable membrane which may have different physical and chemical characteristics, porosities and molecular weight cut off MWCO values but with desired large pore size, may allow drainage of the serosanguinous fluid only to a third layer and to be taken away from the wound site via a plurality of third layer micro-channels. This is optional though.

The third panel of the artificial skin is optional. The third panel is disposed adjacent and coplanar to the second panel. The third panel provides a plurality of third layer micro-channels separated from the second panel via a second semi-permeable membrane which may have different physical and chemical characteristics, porosities and molecular weight cut off MWCO values that only allow non cellular components to pass through. The third layer micro-channels are attached to special input that generates a positive pressure to prevent loss of precious plasma from the wound. This elevated atmospheric pressure will counterbalance the hydrostatic pressure thereby preventing excessive precious plasma loss drastically. It should be noted that periodic cleansing and flushing of the cellular components which can occur manually or automatically via programmed micropumps will have some associated loss of some plasma, however this is negligible in comparison to current modalities which is used-wrapping the wound with absorbable gauze.

The Microfluidic-Based Artificial Skin described above, is combined with micro-plasma technology operating in either O2 or air. To achieve this, embedded metallic electrodes are placed in an inert and biocompatible polymer for microfluidic manufacturing such as PDMS or other dielectric materials that make up the proposed microfluidic device. They are then connected to external power supplies of low wattage such as 1-3 Watts that can be powered by relatively small, portable electrical supplies such as batteries.

The micro-plasma created in this manner is located in the areas neighboring to the electrode/dielectric surface and are typically on the order of ~1 mm in thickness. The micro-plasma generated contains plentiful quantities of important reactive oxygen and nitrogen species (RONS) that are known to play important roles in wound healing, including but not limited to antimicrobial action, enhancing blood flow, attracting cytokines, etc.

Figure 8:
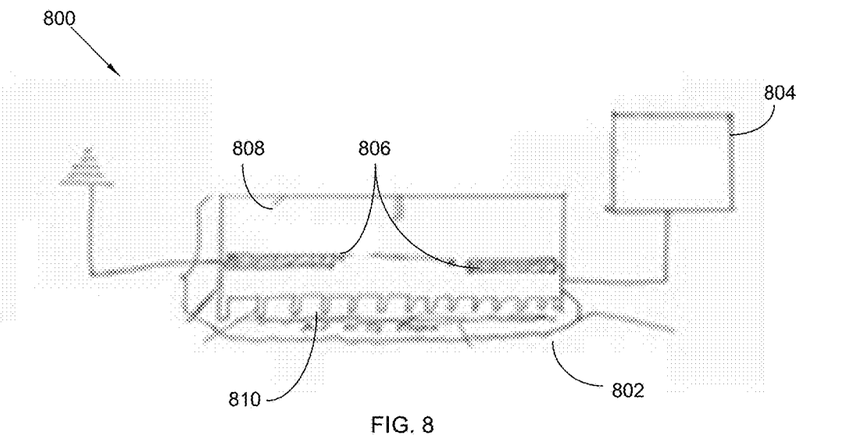
FIG. 8 illustrates a first embodiment of artificial skin with cold plasma capacity. This illustrates the first structure that is designed based on surface micro-discharge (SMD) configuration. In these configurations, the active micro-plasma (ions, electrons) generated at the surface micro-discharge does not come in contact or touch the treated wound surface. Rather, the reactive oxygen and nitrogen species (RONS) created in the thin plasma zone near the dielectric surface disperse and diffuse to the wound surface.
Figure 9:
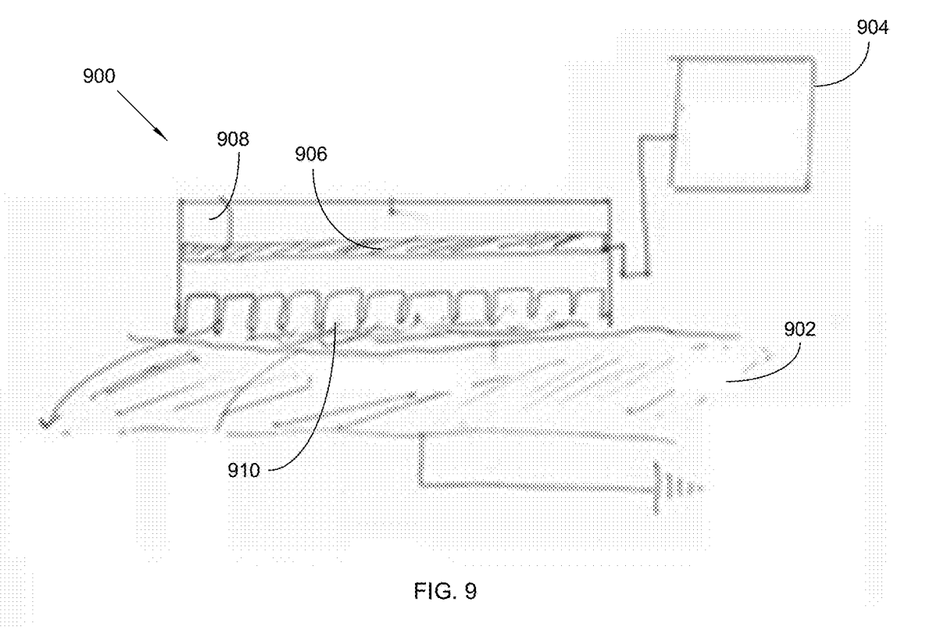
FIG. 9 illustrates a second embodiment of artificial skin with cold plasma capacity. This illustrates the second structure is designed based on a floating electrode dielectric barrier discharge can be designed. In this case, small, transient plasma filaments are created between the dielectric surface and the wound or patient's body, which are acting as a type of floating ground electrodes.

The two typical structures are designed that can be used with either air or O2 to generate the micro-plasmas which are shown schematically in FIGS. 8 and 9.

FIG. 8 shows the first structure that is designed based on surface micro-discharge (SMD) configuration. In these configurations, the active micro-plasma (ions, electrons) generated at the surface micro-discharge does not come in contact or touch the treated wound surface. Rather, the reactive oxygen and nitrogen species (RONS) created in the thin plasma zone near the dielectric surface disperse and diffuse to the wound surface.

FIG. 9 shows the second structure is designed based on a floating electrode dielectric barrier discharge can be designed. In this case, small, transient plasma filaments are created between the dielectric surface and the wound or patient's body, which are acting as a type of floating ground electrodes.

If the gas region near the wound is pure O2, then the plasma will create mostly O3, although the presence of H2O from the wound may create some OH, leading to H2O2, as well. In the case of air, O2 will be the dominant product at low powers (~<0.5 W/cm2), but at higher powers, various oxides of nitrogen will appear (e.g. NO, NO2, HNO3, etc.). Depending on the conditions and desired effects either or both of these configurations and/or chemistry can be helpful in wound healing.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112.

In one embodiment of the present invention presented in FIGS. 1-9, a scalable microfluidic based artificial skin 100 is configured to cover a variety of wounds on natural skin 200 while also providing efficient healing of the wounds. The artificial skin 100 is comprised of a plurality of microfluidic panels 102, 116 separated by semi-permeable membranes which may have different physical and chemical characteristics, porosities and molecular weight cut off MWCO values 108, and also comprising a plurality of micro-pumps and micro-channels 104, 118 for carrying different types of fluids and solutions containing drugs, analgesic, macro- and micro-nutrient, growth factors, etc., for promoting and supporting healing processes 202 in proximity to the wound on the natural skin 200, and for carrying contaminants 204 and cellular components and debris away from the wound.

Figure 1:
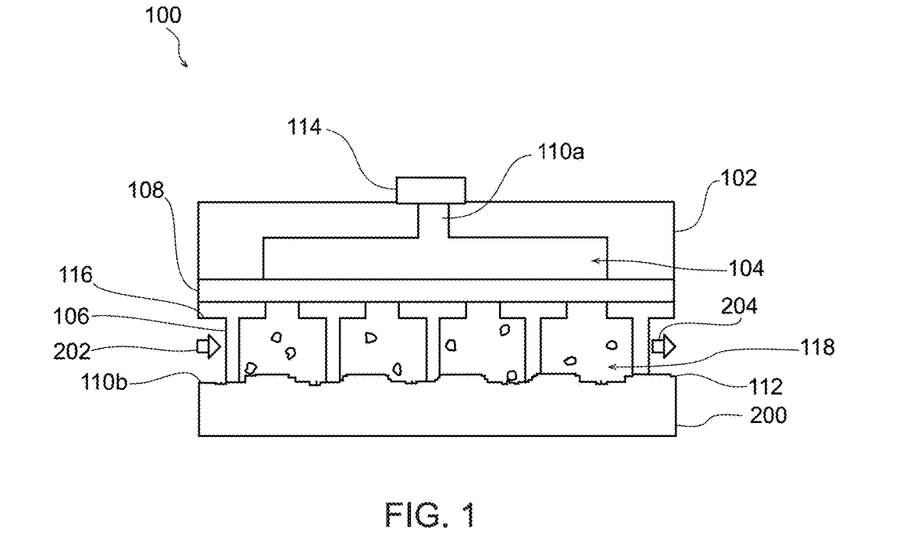
FIG. 1 illustrates a perspective view of an exemplary artificial skin with a valve for an inlet port closed to restrict passage of treatment fluids and solutions including but not limited to antibiotics, analgesics, both macro- and micro-nutrients growth factors, oxygen, and etc., in accordance with an embodiment of the present invention.
Figure 2:
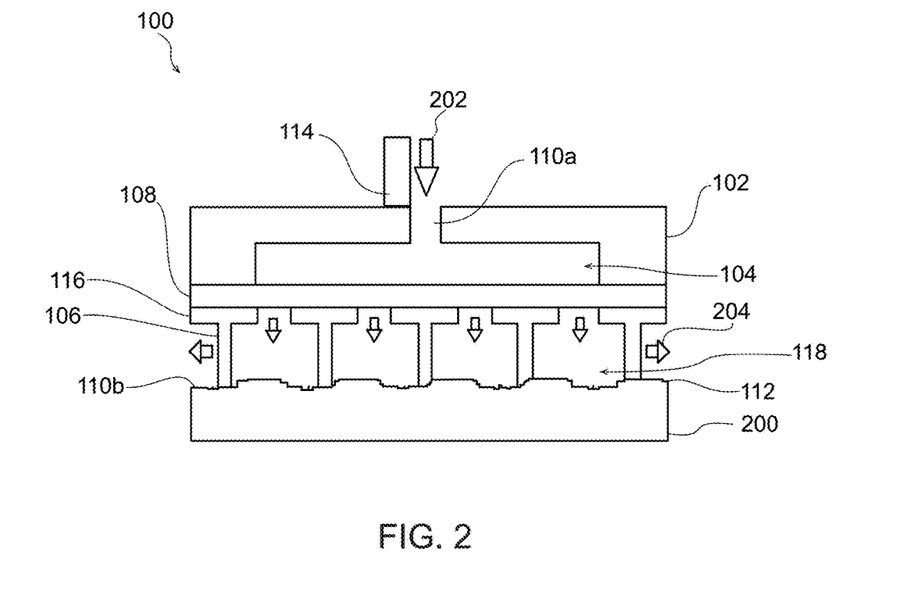
FIG. 2 illustrates a perspective view of an exemplary artificial skin with a valve for an inlet port open to enable entry of treatment fluids and solutions including but not limited to antibiotics, analgesics, both macro- and micro-nutrients growth factors, oxygen, and etc. through micro-channels, in accordance with an embodiment of the present invention.

In one embodiment referenced in FIGS. 1 and 2, a first panel 102 engages the skin and utilizes a plurality of large micro-channels 104 that carry away contaminants 204 and cellular components and debris away from the wound. The first panel 102 further comprises a plurality of micro-pillars 106 that partially elevate the first panel 102 off the natural skin 200 to allow space for cell growth required for proper natural skin 200 healing.

A second panel 116 is disposed adjacent to, and coplanar to the first panel 102. The second panel 116 includes a plurality of small micro-channels 118. The small micro-channels 118 work to irrigate and oxygenate the wound by carrying different types of fluids and solutions for proper healing such as treatment fluids and solutions including but not limited to antibiotics, analgesics, both macro- and micro-nutrients growth factors, oxygen, and etc. 202 to the wound. A first semi-permeable membrane which may have different physical and chemical characteristics, porosities and molecular weight cut off MWCO values 108 separates the first and second panels 102, 116, and inhibits passage of cellular components and debris therebetween.

An optional third panel (not shown) is disposed adjacent to and coplanar to the second panel 116. A second semi-permeable membrane which may have different physical and chemical characteristics, porosities and molecular weight cut off MWCO values separates the second and third panels, and enables passage of non-cellular components between the second panel 116 and the third panel. The panels 102, 116 are disposed in a layered configuration, so as to perform independent functions for promoting and supporting the processes involved in healing the wound. For example, the panels 102, 116 have microfluidic components for enhanced transmission of fluids and debris and enablement of efficient and proper cellular healing.

In some embodiments, the artificial skin 100 forms a detachable patch that covers the wound. The artificial skin 100 may be manufactured from inert and biocompatible polymers used in microfluidics; and thereby compatible with natural skin 200 and wounds thereof. The panels 102, 116 that make up the artificial skin 100 are fabricated from different inert and biocompatible polymers and compounds used in manufacturing microfluidics such as polymeric organosilicon compound like Polydimethylsiloxane (PDMS). The PDMS may be impregnated with silver nanocrystalline powder or other antimicrobial agents, which imparts antibacterial properties to the artificial skin 100.

As illustrated in FIG. 1, a first semi-permeable membrane which may have different physical and chemical characteristics, porosities and molecular weight cut off MWCO values 108 and a second semi-permeable membrane. The second semi-permeable membrane is not shown and may have different physical and chemical characteristics, porosities and molecular weight cut off MWCO values. The second semi-permeable membrane is configured to regulate passage of fluids, cellular components, and debris between the panels. A plurality of micro-pumps and micro-channels 104, 118 carry irrigation fluids, oxygen, and treatment fluids and solutions including but not limited to antibiotics, analgesics, both macro- and micro-nutrients growth factors, oxygen, and etc. 202 through the wound in the artificial skin 100. Further, the artificial skin 100 can keep track of all the fluids (inputs, outputs) that enter and leave the device in order to closely monitor the fluid 202 loses. To optimize wound healing, all the irrigation fluids and solutions such as treatment fluids and solutions including but not limited to antibiotics, analgesics, both macro- and micro-nutrients growth factors, oxygen, etc. may be warmed up to desired temperature prior to entering the micro-channels 104, 118 in the artificial skin 100.

The artificial skin 100 is effective for covering a variety of wounds, and especially a burn wound, while also providing efficient healing of the chronic and non-healing wounds. The artificial skin 100 is scalable and provides a protective barrier and covering for many types of wounds while providing many features that are designed to promote and enhance the wound healing. The artificial skin 100 can be easily applied to many types of wounds as well as a burn wound and securely maintained in place using several engineering solutions such as vacuum generation at the borders and other simple yet innovative processes. By applying this artificial skin 100, a provider will be able to achieve the following goals which are vital for the rapid and complete wound healing. These objectives are as follows:

The artificial skin 100 device utilizes the cutting-edge and highly advanced microfluidic technology which allows it to not only be portable, but have a significantly smaller size and footprint. Furthermore, this scalable and adjustable skin barrier, allows for a close-system which also allows close visual monitoring of the wound via its transparent nature, and provide the ability for strict management of fluids and other modalities that are vital and required for wound support, maintenance and proper repair.

Those skilled in the art will recognize that the artificial skin 100 not only provides novel effective temporary coverage of wounds, providing an effective barrier. However, the artificial skin 100 can also change the paradigm of wound management. By supporting the wound with different type of fluids and solutions containing but not limited to analgesics, antimicrobials, macro and micro-nutrients, growth factors and biologic substances, the artificial skin 100 helps augment or modulate the wound healing processes. And finally using positive pressure oxygen treatment, the artificial skin 100 provides additional assistance to the above wound healing modalities, especially in chronic wounds and non-healing wounds not responding to other treatment.

In addition, using microfluidic micro-channels 104, 118 and fluid regulating valves 114, that are bio-mimetically designed enables the treating healthcare providers to keep the wound constantly covered and uninterrupted and act as a barrier while also retaining the capacity to allow visually monitoring the wound and other functions but not limited to irrigating the wound and removal of excess fluid 202 or contaminants 204 if necessary. Further, all the above mentioned fluids and solutions used for improving the healing processes 202 can be infused for continuous or intermittent irrigation as desired. Additionally the micro-channels 118 in the second panel 116 is configured to automatically measure inflow and outflow of treatment fluids and solutions including but not limited to antibiotics, analgesics, both macro- and micro-nutrients growth factors, oxygen, etc., for precise fluid management, and preventive loss of invaluable and precious vital serum proteins from the wound bed. This recording of flow is possible by applying a positive pressure at the site of the wound negating the hydrostatic pressure in the exposed capillaries. This will also enable keeping the wound area moist at all times as well as oxygenating the wound in contrast to commonly used negative pressure wound-vac.

As shown in FIG. 2, the artificial skin 100 is fabricated from different inert and biocompatible polymers and compounds used in manufacturing microfluidics such as polymeric organosilicon compound, such as PDMS. The PDMS is generally inert and biocompatible material, belonging to a group of polymeric organosilicon compounds that are commonly referred to as silicones. Those skilled in the art will recognize that PDMS is optically clear, and, in general, inert, non-toxic, and non-flammable. The PDMS may be impregnated with nanocrystalline silver or other antimicrobial agents, which gives the artificial skin 100 a property to prevent bacterial growth.

Those skilled in the art will recognize that PDMS is one of the preferred material for molding microfluidic devices. The production by molding of a PDMS microfluidic chip allows mass production of microfluidic chips from a mold. Initially, a mixture of PDMS (liquid) and cross-linking agent (to harden the PDMS) is poured into the mold and placed in a furnace. Once the PDMS is hardened, it can be taken out of the mold. We obtain a replica of micro-channels in PDMS. The completion of the microfluidic device.

FIGS. 3-6 illustrate a few examples of various patterns of many possible patterns for the microfluidic components in artificial skin 100. These patterns illustrate the structure that allow for uniform microfluidic loading among the micro-channels 104, 118 in a skin matrix, since the fluidic resistance along the pathway for each micro-channel from input to output is the same. As a result, the entire area of the artificial skin 100 is uniformly loaded, leading to an efficient healing function. In one embodiment, the micro-channels 104, 118 comprise a binary dendritic architecture.

Figure 3:
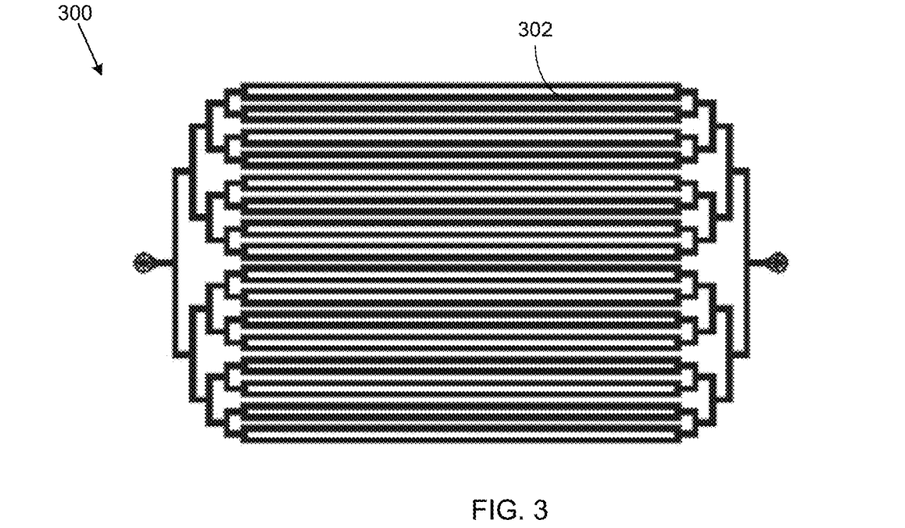
FIG. 3 illustrates an artificial skin having an exemplary parallel pattern of micro-channels, in accordance with an embodiment of the present invention.
Figure 4:
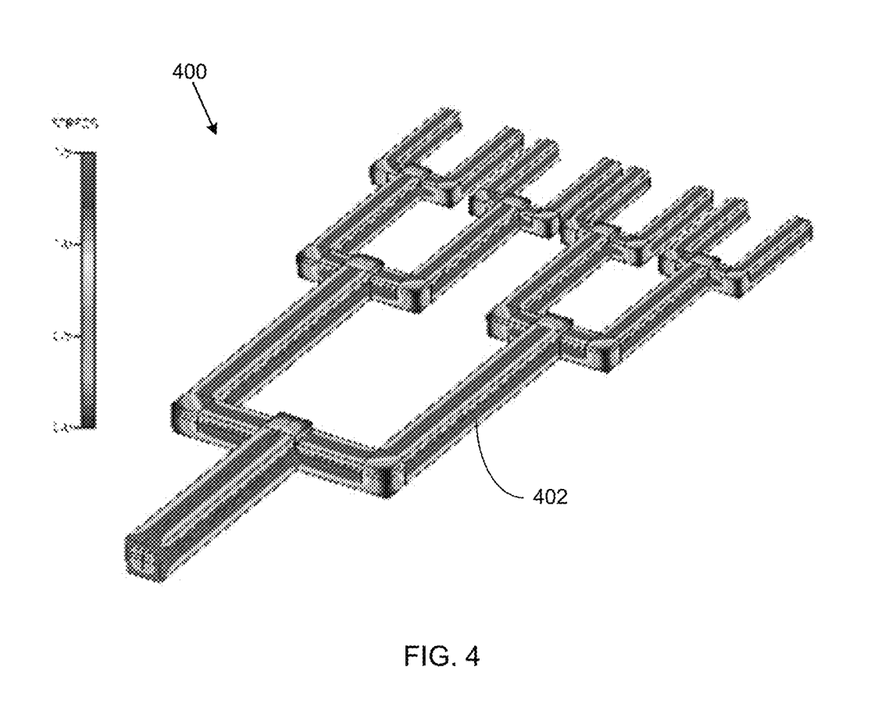
FIG. 4 illustrates an artificial skin having an exemplary a branched pattern, in accordance with an embodiment of the present invention.
Figure 5:
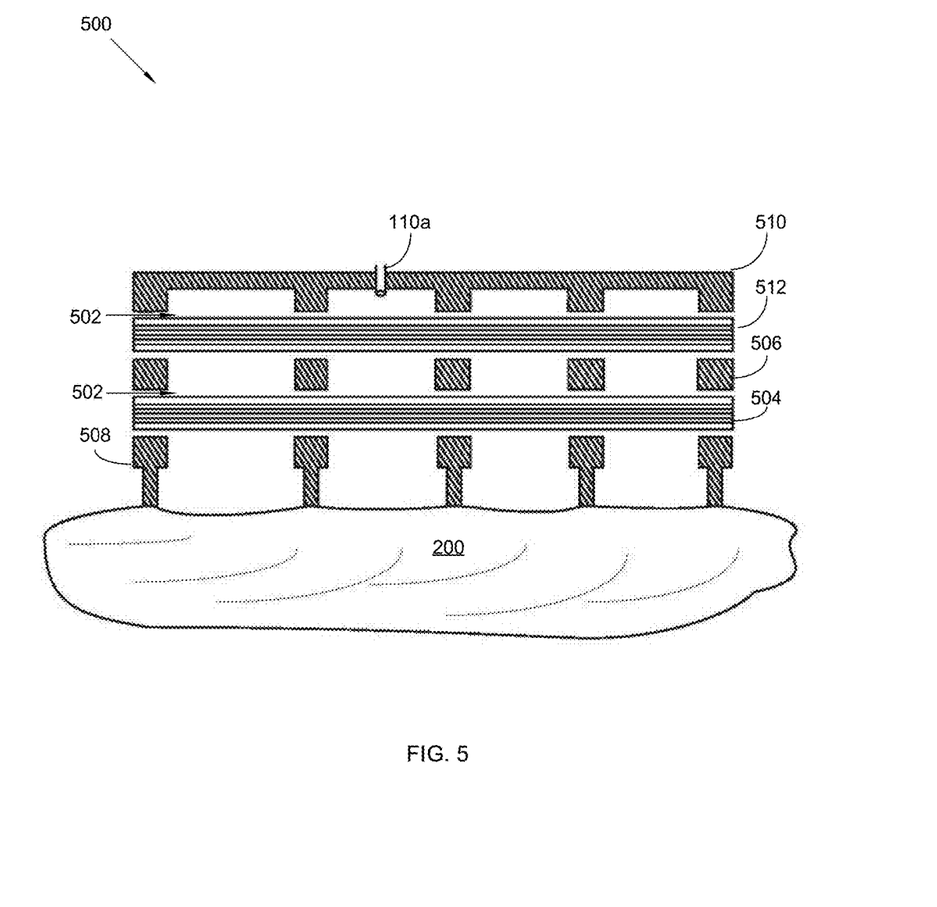
FIG. 5 illustrates an artificial skin having an exemplary a stacked pattern, in accordance with an embodiment of the present invention.

For example, FIG. 3 illustrates a parallel pattern 300 of micro-channels 302. FIG. 4 illustrates a branched pattern 400 of micro-channels 402. FIG. 5 illustrates a stacked pattern 500 of micro-channels 502. FIG. 5 also includes a first panel 504, a second panel 506, and a semipermeable membrane layer 512. A plurality of micro-pillars 508 support the first panel 504 on the second panel 506, and a third panel 510. There is no diffusion possible between the first panel 504 and the second panel 506. However, the second layer channels 502 are closed off with the same material. Further, the semipermeable membrane layer 512 is a different material than the first panel 504 and second panel 506. This is because it is the semipermeable membrane 512 that separates the first panel 504 and the second panel 506 and additional layers or panels in the artificial skin.

Figure 6:
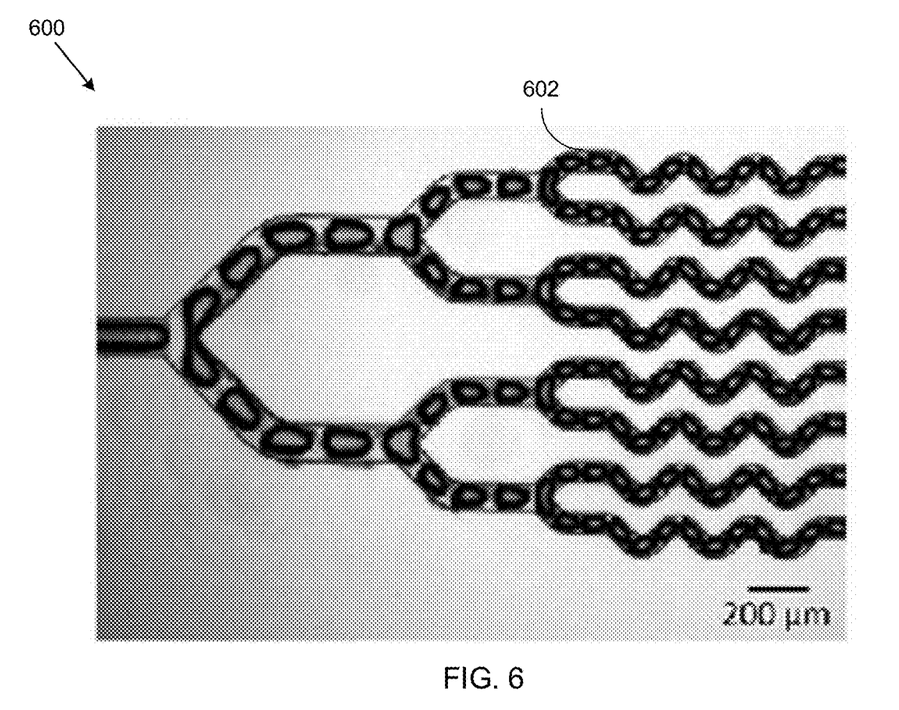
FIG. 6 illustrates an artificial skin having an exemplary a microvasculature pattern, in accordance with an embodiment of the present invention.

FIG. 6 illustrates a microvasculature pattern 600 of micro-channels 602. It is significant to note that the micro-channels 602 in the microvasculature pattern 600 can have dimensions of ten to several hundred micrometers in diameter.

In final construction of the PDMS microfluidic artificial skin 100, the architecture is optimized to maximize the micro-channel area contacting the wound, as a fraction of the total area of the device. Those skilled in the art will recognize that microfluidic aspect ratios in PDMS panels predicts 40-100 μm-wide separations between 100-500 μm-wide and 10-50 μm-tall channels would be adequate to offer high coverage and fast diffusion and distribution of irrigation materials while avoiding channel collapse.

Figure 7:
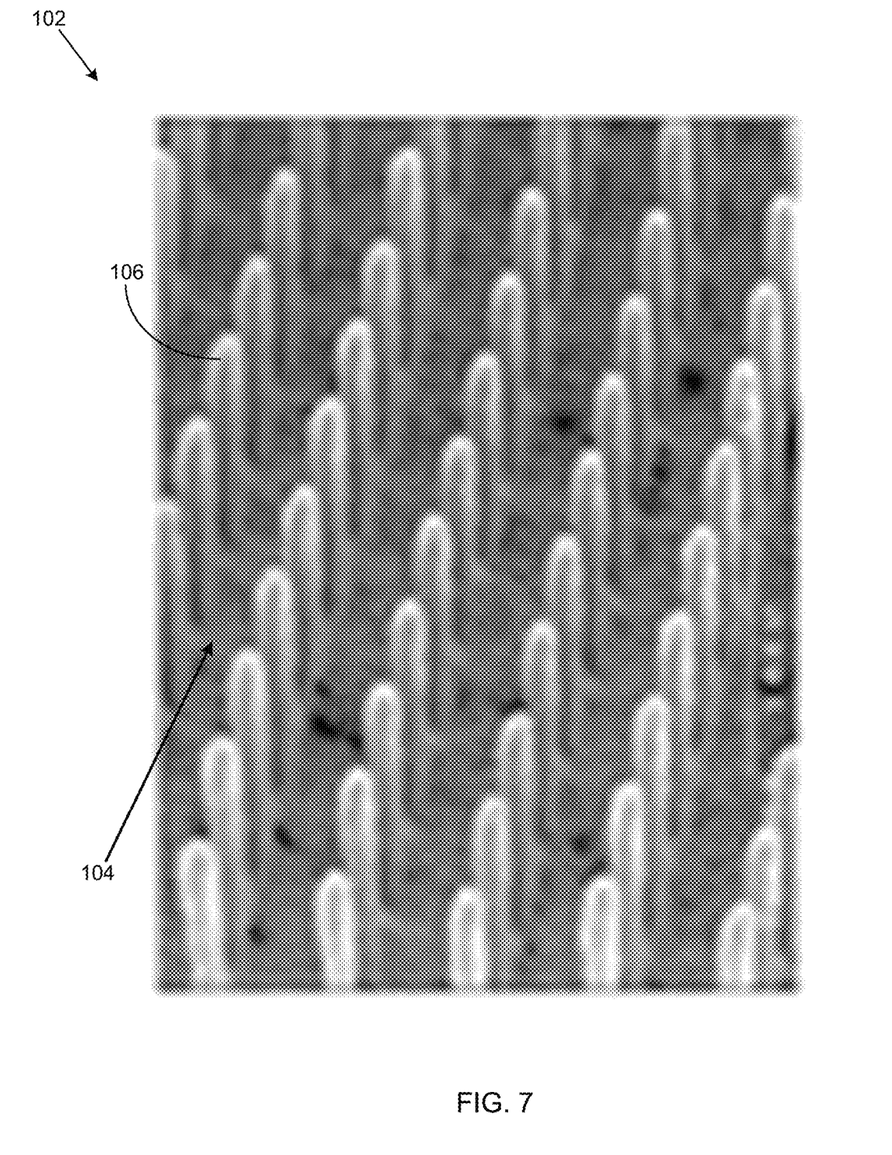
FIG. 7 illustrates an exemplary first panel having a plurality of micro-pillars, in accordance with an embodiment of the present invention.

As illustrated in FIG. 7, the first panel 102 is fabricated from different inert and biocompatible polymers and compounds used in manufacturing microfluidics such as PDMS which could be impregnated with silver nanocrystalline or other antimicrobial agents. The first panel 102 may have a plurality of micro-pillars 106 with varying, but specified width and length. The micro-pillars 106 extrude from the surface to keep the surface of the first panel 102 just slightly above the wound bed, and to allow the fluids and solutions as well as cells and debris to flow through a plurality of large micro-channels 104. The formed micro-pillars 106 are in contact with the wound bed and are the true point of contact between the wound and the artificial skin 100.

Thus, the first panel 102 utilizes a plurality of large micro-channels 104 that are configured to carry contaminants 204 and cellular debris and component away from the wound in the natural skin 200. The large micro-channels (still micron size) are formed into a wider channels for carrying away the contaminants 204, such as during debridement. In one embodiment, the plurality of large micro-channels 104 are configured to record the flow of the contaminant 204 and cellular debris and components.

The first panel 102 may also be used as a trap for the cellular elements of the serosanguinous fluid and have one or several special inlet ports 110$a$, 110$b$ and outlet ports 112 that can be used to exert a slight to neutral negative pressure for the accumulation of these cellular components. In addition, the inlet port(s) 110$a$, 110$b$ and the outlet port(s) 112 may be used to periodically wash the contaminant 204 and cellular debris and components away from the site of the wound via flushing with special fluid or solutions 202, such as a pH balanced isotonic solution, lactated ringers, or sodium bicarbonate which could be medicated as needed.

As described above, the first panel 102 partially engages the natural skin 200. The first panel 102 requires a plurality of large micro-channels. The micro-channels 104 have different dimensions and aspect ratios, as well as designs to ensure easy removal of cellular debris and irrigating fluids and solutions. Further, minimizing contact between the natural skin 200 and the artificial skin 100 is achieved through use of a plurality of micro-pillars 106, or spaced narrow structural supports.

To fulfill the requirements of the first panel 102, the first panel 102 comprises SU8 photoresists designed to produce structures of ~200 micron heights (e.g. SU8-2200). The photoresist are deposited onto a silicon wafer, then patterned using a printed transparency mask, and then developed to produce the mold for the first panel 102. Since multiple heights are required, including vertical access across the artificial skin 100, hybrid molds are produced by use of a second photoresist, e.g. AZ-50. When deposited onto the mold, ultraviolet exposed through the appropriate mask, and developed, this photoresist will leave another layer of photoresist on the mold.

Those skilled in the art will recognize that the hybrid molding process is well established (see Kartalov et al., PNAS, 2006). Uncured PDMS pre-polymer mixture in the usual 10:1 ratio of components may be deposited onto the mold by spinning on a spin coater at angular velocity sufficient to remove enough material to expose the upper ends of the mold. Those skilled in the art will recognize that this process is well established (see Kartalov et al. PNAS 2006). Then the structure is cured by baking at 80° Celsius for 1 hour. Peeking off the PDMS from the mold produces the first panel 102 of the PDMS device, as shown in FIGS. 1 and 2. The first panel 102 has horizontal micro-channels for debridement and vertical micro-channels to connect through the membrane to the medication and support fluid micro-channels.

The second panel 116 is disposed adjacent and coplanar to the first panel 102. The second panel 116 is also fabricated from PDMS, which may also be impregnated with nanocrystalline silver or other antimicrobial agents. The second panel 116 comprises a plurality of small micro-channels 118 that are generally smaller than the large micro-channels 104 in the first panel 102. The small micro-channels 118 work to irrigate and oxygenate the wound by carrying the healing solutions 202, such as flush solution and oxygen.

In one embodiment, the plurality of small micro-channels 118 are configured to record the flow rate of the treatment fluids and solutions including but not limited to antibiotics, analgesics, both macro- and micro-nutrients growth factors, oxygen, and etc. 202. A first semi-permeable membrane which may have different physical and chemical characteristics, porosities and molecular weight cut off MWCO values separates the second panel 116 from the first panel 102. The first semi-permeable membrane which may have different physical and chemical characteristics, porosities and molecular weight cut off MWCO values 108 inhibits passage of the cells and debris between the first and second panels 102, 116.

In one embodiment, the first semi-permeable membrane which may have different physical and chemical characteristics, porosities and molecular weight cut off MWCO values 108 with large pore size and higher MWCO values. The first semi-permeable membrane may allow drainage of the serosanguinous fluid only to a third layer and to be taken away from the wound site via a plurality of third layer micro-channels. In another embodiment, the first semi-permeable membrane 108 which may have different physical and chemical characteristics, porosities and molecular weight cut off MWCO values.

For the second panel 116, a second mold is produced. This structure will have a system of small micro-channels 118 that are used to change treatment fluids and solutions including but not limited to antibiotics, analgesics, both macro- and micro-nutrients growth factors, oxygen, and etc. 202 using a binary dendritic architecture to ensure uniform distribution of medication and change treatment fluids and solutions including but not limited to antibiotics, analgesics, both macro- and micro-nutrients growth factors, oxygen, and etc. 202. Those skilled in the art will recognize that the binary dendritic architecture structure is well understood and has been in wide use in microfluidics for many years (see Kartalov et al, BioTechniques, 2006). Similar to the first panel 102, fabrication of the second panel 116 requires use of printed transparencies for ultraviolet masking of the SU8 photoresist deposited on a silicon wafer.

Following a similar process to the one outlined above, a mold is produced for the second panel 116. The first and second panels 102, 116 may then be assembled together with a semi-permeable membrane which may have different physical and chemical characteristics, porosities and molecular weight cut off MWCO values sandwiched between them. In one possible embodiment, the first and second panels 102, 116 are bonded together by exposure to oxygen plasma just before assembly. The oxygen plasma leaves free radicals on the surface, so that contacting the two surfaces of the panels 102, 116 results in covalent bonding across the surface boundary. Those skilled in the art will recognize that this is a proven and reliable way to ensure bonding between PDMS panels 102, 116 and has been in wide use in microfluidics for many years (see Kartalov, J Nanoscience NanoTech, 2006).

The third panel is optional. The third panel is disposed adjacent and coplanar to the second panel 116. The third panel provides a plurality of third layer micro-channels (not shown) separated from the second panel 116 via a second semi-permeable membrane which may have different physical and chemical characteristics, porosities and molecular weight cut off MWCO values that only allows molecules of certain size and non-cellular components to pass through. The third layer micro-channels are attached to special inlet ports 110a, 110b that generates a positive pressure using oxygen or air to prevent loss of precious plasma from the wound. This elevated atmospheric pressure will counterbalance the hydrostatic pressure thereby preventing too much precious plasma loss drastically. It should be noted that periodic cleansing and flushing of the cellular components will have some associated loss of plasma, however this is negligible in comparison to current modalities which is used-wrapping the wound with absorbable gauze.

The artificial skin 100, as described above, utilizes at least one inlet port 110a, 110b for enabling entry of treatment fluids and solutions including but not limited to antibiotics, analgesics, both macro- and micro-nutrients growth factors, oxygen, and etc. 202, such as irrigating fluid, cleansing fluid, topical nutritional support fluid and oxygen. At least one outlet port 112 is configured to discharge contaminants 204 and cellular debris and components, including fluid and wound exudate respectively. The at least one inlet port 110a, 110b is configured to accommodate standard IV sets, while the at least one outlet port 112 may be connected to a drainage bag which may be emptied through a tap. All ports 110a, 110b, 112 can be closed off when not in use through a valve 114. In one embodiment, the inflows though the inlet port 110a, 110b may be connected to small programmable micro-pumps.

Through the various micro-channels 104, 118, the input and output of fluids, solutions and supportive fortified and/or medicated fluids, such as the inflow isotonic fluid, and outflow serosanguinous and plasma fluid can be recorded accurately. This unique feature helps enhance fluid management while a wound heals without interruptions. These inflow and outflow monitoring can be done automatically and record the input/output for easy access by a medical professional. In one embodiment, the artificial skin 100 utilizes a top down approach. The inflow into the panels 102, 116 is via the inlet port 110a, 110b. The intake is divided in successive steps to provide a network of micro-channels to distribute the oxygen, fluids, medications, analgesics, growth factors, antimicrobials and nutrients in a coordinated and uniform pattern.

The small and third layer microfluidic channels 118 described above may be used to infuse the (change) treatment fluids and solutions including but not limited to antibiotics, analgesics, both macro- and micro-nutrients growth factors, oxygen, and etc. 202 into the wound of the natural skin 200. A plurality of micro-pumps may be used to force the treatment fluids and solutions including but not limited to antibiotics, analgesics, both macro- and micro-nutrients growth factors, oxygen, and etc. 202 through the micro-channels in the respective panels. The change in treatment fluids and solutions including but not limited to antibiotics, analgesics, both macro- and micro-nutrients growth factors, and oxygen may include, without limitation: 1) Debriding agents; 2) Cleansing agent; 3) Antibiotics; 4) Mild anesthetic solution for pain/numbing; 5) Irrigation/flushing of the wound without removing the covering/artificial skin; 6) Temperature adjustment; and 7) Oxygen for enabling oxygenation of the wound.

Those skilled in the art will recognize that there are two common methods by which fluid actuation through the micro-channels 104, 118 can be achieved: pressure driven flow and electro-kinetic flow. In pressure driven flow, in which the fluid is pumped through the device via positive displacement pumps, such as syringe pumps. One of the basic laws of fluid mechanics for pressure driven laminar flow, the so-called no-slip boundary condition, states that the fluid velocity at the walls must be zero. This produces a parabolic velocity profile within the channel. The parabolic velocity profile has significant implications for the distribution of molecules transported within a channel. Pressure driven flow can be a relative inexpensive and quite reproducible approach to pumping fluids through micro-devices. With the increasing efforts at developing functional micro-pumps, pressure driven flow is also amenable to miniaturization.

Another common technique for pumping fluids is that of electro-osmotic pumping. If the walls of a microchannel have an electric charge, as most surfaces do, an electric double layer of counter ions will form at the walls. When an electric field is applied across the channel, the ions in the double layer move towards the electrode of opposite polarity. This creates motion of the fluid near the walls and transfers via viscous forces into convective motion of the bulk fluid. If the channel is open at the electrodes, as is most often the case, the velocity profile is uniform across the entire width of the channel. However, if the electric field is applied across a closed channel (or a back-pressure exists that just counters that produced by the pump), a recirculation pattern forms in which fluid along the center of the channel moves in a direction opposite to that at the walls. In closed micro-channels, the velocity along the centerline of the channel is 50% of the velocity at the walls.

In one possible embodiment, the artificial skin 100 is in the form of a corneal patch. Though the corneal patch is distinct from the artificial skin 100. Those skilled in the art will recognize that the corneal epithelial layer acts as a physical barrier and forms a line of defense to prevent noxious agents from infecting this tissue. Corneal epithelium may be impaired by mechanical or chemical damage or be destroyed by microbial, such as viral, bacterial or fungal, infection. When injuries occur in the surface of the cornea, the corneal epithelium undergoes a wound healing process. Self-regeneration of the epithelium is essential to maintain corneal transparency and normal vision of the human eye. Typically, the healing takes place within 2 to 3 days after wounding of the corneal epithelium. It starts from basal cell renewal via cell division and migration of stem cells from the limbus that flatten and form a new cover on the basement membrane. Then a more pronounced proliferation occurs, resulting in an increase in thickness and formation of its normal layers.

Those skilled in the art will recognize that corneal epithelial cell adhesion and migration likely rely on the extracellular matrix (ECM)-integrin system and are the most important processes during re-epithelialization and wound healing ECM proteins, such as type IV collagen, laminin, and fibronectin, are components of the corneal basement membrane. When corneal injury results in destruction of the basement membrane, fibronectin is synthesized and deposited at the site of the epithelial defect and serves as a temporary matrix for epithelial cell adhesion and migration.

The corneal patch, as used in the present invention, may consist of two parts, 1) A microfluidic and transparent patch with specialized micro-channels and dedicated inflow and outflow ports, 2) Special mini-pumps for coordinating flow of oxygen and fluids as desired and is programmable. Once the corneal patch is placed on top of the cornea, it defines a closed chamber over the cornea wound which has several inlet and outlet ports 110a, 110b, 112 for supply of the irrigating fluid, cleansing fluid, topical anesthetic, and most importantly oxygen delivery of different concentrations as well as escape of the fluid and discharges respectively. The inlet ports 110a, 110b accommodate standard IV set or much smaller caliber tubing, while the outlet port 112 is connected to a drainage bag which may be emptied and discarded easily. All ports 110a, 110b, 112 can be closed off when not in use. All inflows are connected to small programmable pumps.

The corneal patch provides a clean and effective method of applying different solutions (irrigation, cleansing and anesthetics) to the corneal surface. The features of this innovative and uniquely designed patch are as follows:

Provides a closed system for cornea irrigation.

Provides a system for delivery of different partial pressure oxygen

Reduces exposure of the cornea to the atmosphere and external elements

Prevents maceration of the surrounding skin by soggy dressings or fistula effluent.

Provides a system for the evaluation of topical antiseptics, antibiotics, and other solutions In another embodiment, the artificial skin 100 consists of two parts: an adhesive sheet of stomahesive to which is fused the microfluidic and transparent artificial skin 100. The adhesive sheet of stomahesive, once in place, defines a closed chamber over the wound. Those skilled in the art will recognize that stomahesive is a preparation of gelatin, pectin, sodium carboxymethylcellulose, and polyisobutylene that is non-allergenic and sticks avidly to moist skin as a protective cover and to excoriated skin to promote rapid healing.

Thus, the artificial skin 100 (should it be Corneal Patch) provides a clean and effective method of applying and changing different treatment fluids and solutions including but not limited to antibiotics, analgesics, both macro- and micro-nutrients growth factors, oxygen, and etc. 202 and different solutions of antimicrobial, analgesic, growth factors and nutrients used for irrigation, cleansing and nutritional support to the wound surface. The features of the artificial skin 100 to convey the following advantages over conventional dressings include the following:

a) Provides a closed system for wound irrigation.

b) Reduces exposure of the wounds to the atmosphere and eliminates handling of contaminated materials;

c) Prevents maceration of the surrounding skin by soggy dressings or fistula effluent;

d) Eliminates unpleasant smell;

e) Proves cost-effective by saving nursing time spent on change of dressings; and f) Provides a system for the evaluation of topical medications or growth factors, antiseptics, antibiotics, and other solutions or gases in the treatment of sepsis and promotion of wound healing.

Furthermore, since this novel artificial skin 100 can be left in place for a longer period of time, the wound bed is not disturbed, and the patient requires less pain management. Meanwhile, the inert and biocompatible polymers such as PDMS material is highly transparent which would allow visualization of the wound for closer examination and continuous monitoring that is not achieved with other wound covers. Additionally, the use of automated irrigation system of micro-channels and micro-valves 114 would provide the physician the ease of programming the frequency and the length of each one of the multiple basic steps to be performed in a 24 hour. Moreover, any step of application of the artificial skin 100 can be performed on as needed basis as well providing greater flexibility for the healthcare providers.

One exemplary study demonstrates that artificial skin 100 may be an important space for the accumulation of uremic toxins and their local toxicity interfering with wound healing. Those skilled in the art will recognize that the loss of kidney function results in the accumulation of many metabolites, some of which have been identified and their toxic effects on cell metabolism elucidated. Over a hundred of such uremic toxins have been identified, and their removal by various modalities of renal replacement therapy studied. Increasingly, more identified and unidentified putative uremic substances are detected in the plasma of uremic patients, indicating that current knowledge of existing toxins may only represent the tip of the iceberg. Weissinger et al. employed capillary electrophoresis mass spectrometry (CE-MS) and detected 1394 polypeptides. Several other authors have used proteomic techniques to detect and identify proteins and peptides that are retained in the plasma, urine or dialysis effluent of patients with chronic kidney disease. As such, new putative uremic toxins have been identified.

In CKD, most uremic metabolites and toxins are byproducts of cell metabolism. As such, they are expected to be present in ISF due to its proximity to cells, in concentrations that for some metabolites may differ from plasma concentrations. Urea for example has been shown to occur in similar concentrations in plasma and ISF in steady states, but there may be a lag between the two compartments, even for such a small metabolite, during non-equilibrium conditions such as dialysis. Apart from knowledge on urea, data on ISF composition of other uremic toxins is sparse, partly due to methodological limitations in consistently sampling the interstitium. It is conceivable that owing to the small size of the plasma-interstitial capillary pores and the Gibbs-Donnan effect of plasma proteins, larger, less soluble and highly charged molecules may be present in different concentrations between plasma and ISF. ISF therefore presents itself as a potentially interesting fluid candidate for studying uremic toxicity and may reveal yet unknown metabolites or compartmental behaviors of some known toxins. Such compartmental behavior may have important implications for the design and delivery of renal replacement therapies like dialysis in order to achieve optimum toxin clearance as well as local tissue homeostasis and repair.

Microfluidic Artificial Skin with Microdialysis Capability

This unique device is a tool which can act as several important devices simultaneously. This device is:

Dialysis device, using locally improving the local wound milieu in patient with impaired renal function;

A wound cover to protect the exposed tissue and wound from the elements; and

A sampling device of the local wound area that utilizes the principal of diffusion through a semi-permeable membrane which may have different physical and chemical characteristics, porosities and molecular weight cut off MWCO values.

The technology is non-invasive, easy to handle, and can be used for extended period of time extending into several days. Due to its transparency as well as multilayered design, modalities can change as needed in treating chronic Kidney disease patient and others at higher risk of wound dehiscence.

The method is performed by covering the wound area with different inert and biocompatible polymers and compounds used in manufacturing microfluidics such as PDMS which could be impregnated with silver nanocrystalline or other antimicrobial agents such as special PDMS microfluidic wound patch overlaying the wound. The semipermeable membrane (detailed characteristics) used for local wound care and local microdialysis function of comes in direct contact with the soft tissue. The device is connected to a reservoir of biologically sterile dialysate fluid which could have different compositions as needed, which can be programmed to perform local dialysis at the level of the wound. The device is perfused with a sterile isotonic solution of different balance and pH adjusted electrolyte solutions via a small pump attached to its inlet lumen. In the tissue, substances from the interstitial fluid diffuse through the semipermeable membrane which may have different physical and chemical characteristics, porosities and molecular weight cut off MWCO values into the perfusion fluid. The dialysate moves through the microfluidic channels of the device and into a collection reservoir.

Despite recent advancements in micro vascular surgery clinical observation of free flaps is still difficult and time consuming. An early detection of ischemia is crucial for the salvage of the flap. Microfluidic based artificial skin with or without microdialysis function allows continuous monitoring of the wound and grafted tissue.

The Microfluidic-Based Artificial Skin described above, is combined with micro-plasma technology operating in either O2 or air. To achieve this, embedded metallic electrodes are placed in an inert and biocompatible polymer for microfluidic manufacturing such as PDMS or other dielectric materials that make up the proposed microfluidic device. They are then connected to external power supplies of low wattage such as 1-3 Watts that can be powered by relatively small, portable electrical supplies such as batteries.

The micro-plasma created in this manner is located in the areas neighboring to the electrode/dielectric surface and are typically on the order of ~1 mm in thickness. The microplasma generated contains plentiful quantities of important reactive oxygen and nitrogen species (RONS) that are known to play important roles in wound healing, including but not limited to antimicrobial action, enhancing blood flow, attracting cytokines, etc.

The two typical structures are designed that can be used with either air or O2 to generate the micro-plasmas which are shown schematically in FIGS. 8 and 9.

FIG. 8 shows the first structure that is designed based on surface micro-discharge (SMD) configuration. In these configurations, the active micro-plasma (ions, electrons) generated at the surface micro-discharge does not come in contact or touch the treated wound surface. Rather, the reactive oxygen and nitrogen species (RONS) created in the thin plasma zone near the dielectric surface disperse and diffuse to the wound surface.

FIG. 8 illustrates a first embodiment of artificial skin 800 with cold plasma capacity. The artificial skin 800 is designed based on surface micro-discharge (SMD) configuration. In these configurations, the active micro-plasma (ions, electrons) generated at the surface micro-discharge 810 does not come in contact or touch the treated wound surface 802. Rather, the reactive oxygen and nitrogen species (RONS) created in the thin plasma zone near the dielectric surface 808 disperse and diffuse to the wound surface 802. Air and $O_2$ are confined to the wound 802. A power supply 804 creates voltage for the electrodes 806 for generation of the ions and electrons. For the example shown is for a one-layer Artificial Skin 800 though can be applied to multilayered Artificial Skin.

FIG. 9 shows the second structure is designed based on a floating electrode dielectric barrier discharge can be designed. In this case, small, transient plasma filaments are created between the dielectric surface and the wound or patient's body, which are acting as a type of floating ground electrodes.

FIG. 9 illustrates a second embodiment of artificial skin 900 with cold plasma capacity. The second embodiment is designed based on a floating electrode dielectric barrier in which discharge can be designed. In this case, small, transient plasma filaments are created between the dielectric surface or microfluidic substrate 908, such as PDMS, and the wound surface 902 or patient's body, which are acting as a type of floating ground electrodes 906. A nanosecond discharge portion 910 creates $O_2$ or air plasma containing RONS differing in the two areas. A power supply 904 creates voltage for the electrodes 906 for generation of the ions and electrons. For the example shown is for a one-layer Artificial Skin 900 though can be applied to multilayered Artificial Skin.

If the gas region near the wound is pure O2, then the plasma will create mostly O3, although the presence of H2O from the wound may create some OH, leading to H2O2, as well. In the case of air, O2 will be the dominant product at low powers (~<0.5 W/cm2), but at higher powers, various oxides of nitrogen will appear (e.g. NO, NO2, HNO3, etc.). Depending on the conditions and desired effects either or both of these configurations and/or chemistry can be helpful in wound healing.

What I claim is:

1. A scalable microfluidic based artificial skin for covering, and protection while supporting and promoting proper and rapid healing of different types of wounds including chronic wounds and non-healing wounds on natural skin, the artificial skin comprising:
   a first panel, the first panel comprising a plurality of micro-pillars, the plurality of micro-pillars configured to enable support of the first panel on a natural skin, whereby the first panel is configured to partially engage the natural skin, the first panel further comprising a plurality of large micro-channels, the plurality of large micro-channels configured to enable carrying of a contaminant and a cellular component from the natural skin, the first panel defined by a polymeric organosilicon compound, the polymeric organosilicon compound having a nanocrystalline silver compound;
   a second panel, the second panel disposed adjacent and plane-parallel to the first panel, the second panel comprising a plurality of small micro-channels, the plurality of small micro-channels configured to enable carrying of a healing fluid to the natural skin, the second panel defined by the polymeric organosilicon compound, the polymeric organosilicon compound having the nanocrystalline silver compound;
   a first semipermeable membrane, the first semi-permeable membrane disposed between the first panel and the second panel, the first semi-permeable membrane configured to enable inhibition of passage of cells and debris between the first panel and the second panel;
   a third panel, the third panel disposed adjacent and plane-parallel to the second panel, the third panel comprising a plurality of third layer micro-channels, the plurality of third layer micro-channels configured to enable carrying of the healing fluid to the natural skin, the second panel defined by the polymeric organosilicon compound, the polymeric organosilicon compound having the nanocrystalline silver compound;
   a second semipermeable membrane, the second semi-permeable membrane disposed between the second panel and the third panel, the second semi-permeable membrane configured to enable passage of a non-cellular component between the second panel and the third panel;

at least one inlet port, the at least one inlet port configured to enable passage of the healing fluid to the plurality of small micro-channels and the plurality of third layer micro-channels; and an outlet port, the outlet port configured to enable discharge of the contaminant and the cellular component.

2. The artificial skin of claim 1, wherein the artificial skin is a removable patch.

3. The artificial skin of claim 1, wherein the artificial skin is substantially inert and antibacterial.

4. The artificial skin of claim 1, wherein the polymeric organosilicon compound is polydimethylsiloxane.

5. The artificial skin of claim 1, wherein the plurality of large micro-channels are horizontally disposed and vertically disposed.

6. The artificial skin of claim 1, wherein the plurality of large micro-channels are configured to record the flow of the contaminant and the cellular component.

7. The artificial skin of claim 1, wherein the plurality of large micro-channels are configured to enable carrying of the contaminant and the cellular component from a wound in the natural skin.

8. The artificial skin of claim 1, wherein the first semipermeable membrane is a protein membrane.

9. The artificial skin of claim 1, wherein the plurality of small micro-channels and the plurality of large micro-channels comprise a binary dendritic architecture.

10. The artificial skin of claim 1, wherein the plurality of small micro-channels are configured to record the flow of the healing fluid.

11. The artificial skin of claim 1, wherein the first panel and the second panel are bonded together through an oxygen plasma process.

12. The artificial skin of claim 1, wherein the at least one inlet port comprises a valve, the valve configured to regulate passage of the healing fluid.

13. The artificial skin of claim 1, wherein the healing fluid includes at least one member selected from the group consisting of: a debriding agent, a cleansing agent, an antibiotic, an anesthetic solution, a flush solution, and oxygen.

14. The artificial skin of claim 1, further including a plurality of micro-pumps, the plurality of micro-pumps configured to force the healing fluid through the plurality of small micro-channels, the plurality of micro-pumps further configured to force the contaminant and the cellular component through the plurality of large micro-channels.

15. A scalable microfluidic based artificial skin for covering, and protection while supporting and promoting proper and rapid healing of different types of wounds including chronic wounds and non-healing wounds on natural skin, the artificial skin comprising:

a first panel, the first panel comprising a plurality of micro-pillars, the plurality of micro-pillars configured to enable support of the first panel on a natural skin, whereby the first panel is configured to partially engage the natural skin, the first panel further comprising a plurality of large micro-channels, the plurality of large micro-channels configured to enable carrying of a contaminant and a cellular component from the natural skin, the first panel defined by a polymeric organosilicon compound, the polymeric organosilicon compound having a nanocrystalline silver compound;

a second panel, the second panel disposed adjacent and plane-parallel to the first panel, the second panel comprising a plurality of small micro-channels, the plurality of small micro-channels configured to enable carrying of a healing fluid to the natural skin, the second panel defined by the polymeric organosilicon compound, the polymeric organosilicon compound having the nanocrystalline silver compound;

a first semipermeable membrane, the first semi-permeable membrane disposed between the first panel and the second panel, the first semi-permeable membrane configured to enable inhibition of passage of cells and debris between the first panel and the second panel;

at least one inlet port, the at least one inlet port configured to enable passage of the healing fluid to the plurality of small micro-channels; and an outlet port, the outlet port configured to enable discharge of the contaminant and the cellular component.

16. The artificial skin of claim 15, wherein the polymeric organosilicon compound is polydimethylsiloxane.

17. The artificial skin of claim 15, wherein the plurality of large micro-channels are configured to record the flow of the contaminant and the cellular component.

18. The artificial skin of claim 15, wherein the plurality of small micro-channels are configured to record the flow of the healing fluid.

19. The artificial skin of claim 15, wherein the plurality of small micro-channels and the plurality of large micro-channels comprise a binary dendritic architecture.

20. The artificial skin of claim 15, further including a plurality of micro-pumps, the plurality of micro-pumps configured to force the healing fluid through the plurality of small micro-channels, the plurality of micro-pumps further configured to force the contaminant and the cellular component through the plurality of large micro-channels.

21. The artificial skin of claim 15, further including a corneal patch.

22. The artificial skin of claim 15, wherein the artificial skin is configured with microdialysis capability, wherein the microdialysis is configured to use a dialysate.

23. The artificial skin of claim 22, wherein the microdialysis is operable on a side of a tissue.

24. The artificial skin of claim 23, wherein the artificial skin is configured to perform cold-plasma.

25. The artificial skin of claim 24, wherein the cold plasma includes at least one of the following: a power supply, an electrode, a microfluidic substrate, and a nanosecond discharge at a wound surface.

* * * * *